US008168254B2

(12) United States Patent
Dovertie et al.

(10) Patent No.: US 8,168,254 B2
(45) Date of Patent: May 1, 2012

(54) METHOD AND ARRANGEMENT FOR SYNCHRONIZED POSITIONING OF AT LEAST ONE ESSENTIALLY CONTINUOUS MATERIAL WEB BASED ON A VIRTUAL MASTER FUNCTION

(75) Inventors: Ralph Dovertie, Västra Frölunda (SE); Anders Norder, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 832 days.

(21) Appl. No.: 12/297,555

(22) PCT Filed: Apr. 27, 2006

(86) PCT No.: PCT/SE2006/000515
§ 371 (c)(1),
(2), (4) Date: Oct. 17, 2008

(87) PCT Pub. No.: WO2007/126345
PCT Pub. Date: Nov. 8, 2007

(65) Prior Publication Data
US 2009/0176008 A1    Jul. 9, 2009

(51) Int. Cl.
*B05D 7/00* (2006.01)
*B05C 11/00* (2006.01)
(52) U.S. Cl. ........... 427/172; 427/176; 118/33; 118/712
(58) Field of Classification Search ............... 427/172, 427/176; 118/33, 712
See application file for complete search history.

(56) References Cited

U.S. PATENT DOCUMENTS

| | | | |
|---|---|---|---|
| 3,556,509 | A | 1/1971 | Crum |
| 4,837,715 | A | 6/1989 | Ungpiyakul et al. |
| 5,779,233 | A | 7/1998 | Schweiger |
| 6,354,984 | B1 | 3/2002 | Hensley et al. |
| 6,869,386 | B2 | 3/2005 | Lamping et al. |
| 6,957,160 | B2 * | 10/2005 | Miller et al. ............ 702/94 |
| 2004/0005974 | A1 * | 1/2004 | Lamping et al. ......... 493/10 |
| 2005/0125180 | A1 | 6/2005 | Miller et al. |

FOREIGN PATENT DOCUMENTS

| | | |
|---|---|---|
| DE | 1 942 444 | 2/1970 |
| JP | 09-138115 | 5/1997 |
| JP | 10-239019 | 9/1998 |
| JP | 2001-034886 | 2/2001 |
| JP | 2005-080827 | 3/2005 |
| RU | 2 141 924 | 11/1999 |
| WO | WO 88/03089 | 5/1988 |
| WO | WO 98/21136 | 5/1998 |
| WO | WO 99/32384 A1 | 7/1999 |
| WO | WO 99/32385 | 7/1999 |
| WO | WO 00/59429 A1 | 10/2000 |
| WO | WO 2004/002385 A2 | 1/2004 |

OTHER PUBLICATIONS

International Search Report for corresponding application No. PCT/SE2006/000515, completed Nov. 8, 2006.
Written Opinion of the International Searching Authority for corresponding application No. PCT/SE2006/000515.
An English Translation of the Japanese Office Action (Notice of Reasons for Rejection) dated Nov. 30, 2010, issued in the corresponding Japanese Patent Application No. 2009-507619.
Official Action issued in the corresponding Russian Application No. 2008142419.
Supplementary European Search Report issued in the corresponding Application No. 06733370.8-1262 dated Dec. 30, 2009.
An English Office Action (Notice of Reasons for Rejection) dated Jul. 5, 2011, issued in the corresponding Japanese Patent Application No. 2009-507619.

* cited by examiner

*Primary Examiner* — Frederick Parker
(74) *Attorney, Agent, or Firm* — Buchanan Ingersoll & Rooney PC

(57) ABSTRACT

A method for synchronized positioning of a web for manufacturing products. The method includes feeding the web into a production apparatus at a first speed; processing in the production apparatus, with the web being fed forward at a second speed; and detection of each synchronization mark for positioning the respective motif in a predetermined position on each product. The method includes the following steps: generation of a reading of the actual value of a virtual master function upon the detection, which includes a cyclic clock where the number of cycles per product includes an integer; comparison between the actual value and the expected value of the virtual master function; and stretching of the web in response to any deviation between the actual value and the expected value, with the aim of minimizing the deviation.

14 Claims, 2 Drawing Sheets

METHOD AND ARRANGEMENT FOR SYNCHRONIZED POSITIONING OF AT LEAST ONE ESSENTIALLY CONTINUOUS MATERIAL WEB BASED ON A VIRTUAL MASTER FUNCTION

TECHNICAL FIELD

The disclosure relates to a method for synchronized positioning of at least one essentially continuous web of material for manufacturing products that comprise printed motifs or similar processed elements, which said web of material is intended to be divided into nominal division lengths and comprises synchronization marks that recur at regular intervals.

The disclosure also relates to an arrangement for synchronized positioning of at least one essentially continuous web of material for manufacturing products that comprise printed motifs or similar processed elements, which said web of material is intended to be divided into nominal division lengths and comprises synchronization marks that recur at regular intervals.

BACKGROUND ART

A manufacturing process for the production of absorbent products such as diapers, incontinence pads, sanitary towels and panty liners normally comprises a processing of various continuous webs of material, which are fed out from rolls or the like and passed through various work stations for the carrying out of various work elements and process steps. For example, it is common for a manufacturing process for absorbent products to provide a first web of material that defines a backing layer consisting of a plastic film that is non-permeable to liquid and a second web of material that defines an outer layer consisting of a liquid-permeable material, for example a non-woven material. The product can also be provided with other components, such as, for example, an absorbent core of a material intended to absorb bodily fluids.

The work elements that are carried out during a process of the type described above can consist, for example, of attaching together two or more layers of material, perforating, cutting, gluing, embossing a pattern or other type of shaping and processing of the materials involved. Other examples of work elements are the application of different components, such as fastening devices (so called tabs), cellulose centres, elastic material, so-called disposal tapes, etc.

In all, the webs of material in question go through various process steps that result in a continuous complete web of material that consists of a continuous row or strip of a number of absorbent products. Each individual product is finally shaped by this web being cut at regular intervals that correspond to the length of the finished product.

In a process of the type described above, some form of decorative element is often applied, such as a printed pattern or pictures, which are intended to enhance the visual impression of the finished product. Such a printing process is preferably carried out by conventional multi-colour printing. In particular, concerning absorbent products in the form of diapers for babies, such printed motifs, for example in the form of fairy-tale characters and cartoon characters, are considered to make the product more appealing to the consumer. In addition, such a procedure for printing a motif is suitably carried out on the backing layer for a diaper, not least due to the fact that such a backing layer is normally made of a polymer film that is essentially non-permeable to liquid, the surface of which is suitable for colour printing with a good quality and high resolution. In this way, a printed back is obtained on the finished product.

Certain types of printed motif are of such a nature that they can be positioned and oriented in any way on the back of the product. Such a printed motif can then be said to be "unsynchronized" in the sense that it does not need to be positioned in a given and precise way along the back of each product. This can, for example, be the case with an irregular pattern or a motif in the form of abstract symbols, the location of which on the back does not need to have a particular geometrical positioning on the product concerned.

There are, however, other types of printed motifs that can be said to be "synchronized" in the sense that they must be placed in a given position on the layer in question so that each individual product is provided with a print that is always in a predetermined position. An example of such a synchronized print can be a motif that is intended to be printed in the middle of the back of the product, that is centred both longitudinally and laterally.

Against the background of the above, it has been found that there is a need for simple, reliable and cost-effective methods and arrangements which have a high level of precision and with which a synchronized print in the form of patterns, characters and other motifs can be provided on an absorbent article. More specifically, the web of material that carries the print in question is to be synchronized in an arrangement for manufacturing the product in question, so that the various work elements that are carried out on the product are carried out in the correct positions in relation to the printed motif.

A previously known way of obtaining such a synchronized printing process is to utilize previously printed reference marks or synchronization marks, that are suitably positioned at regular intervals on the web of material in question. Each synchronization mark can be printed as a small coloured stripe along the edge of the web of material and can be detected electronically by means of an optical detector. Such synchronization marks are then used to control the manufacturing process for the product concerned so that, in its final position, the motif that is to appear on the finished product is always in the intended position on the finished product.

Patent document WO 00/59429 shows an arrangement that utilizes synchronization marks for controlling the positioning of a printed motif on an absorbent product. According to this document, synchronization marks are provided on such sections of the product that are cut away later during the manufacturing process. In this way, temporary synchronization marks are defined that are removed before the product has been completed.

In addition, document WO 99/32384 shows an arrangement for synchronizing two webs of material during the manufacture of absorbent products. One of these webs of material consists of a backing layer that comprises printed motifs, which are then to be synchronized with an additional web of material that comprises an outer layer and an absorbent core. According to WO 99/32384, a stretching of the backing layer is obtained when required, with the object of synchronizing the two webs of material.

The document US 2005/0125180 shows a system arranged for synchronization of different webs of material that are provided with elements, for example in the form of printed motifs, that are positioned at certain given regular intervals. The position of the respective element can then be detected using, for example, a printed synchronization mark.

It can be pointed out that these known systems are based on a printed motif being synchronized by a synchronization mark being detected and by parameters in a processing apparatus being controlled in response to the position of the respective synchronization mark. This is, however, a relatively complex process, and there is a need for methods and arrangements for improved synchronization of printed motifs and similar elements on absorbent articles of various kinds.

OBJECT AND SUMMARY

A principle object is thus to provide an improved method and arrangement for synchronized positioning of motifs when manufacturing products, taking a continuous web of material as a starting point.

The above object is achieved by a method of the type described in the introduction, which method comprises: generation of a reading off of the actual position (actual value) of a virtual master function upon the said detection, which said master function consists of a cyclic clock where the number of cycles per product, or alternatively the number of products per cycle, consists of an integer; comparison between the said actual position (actual value) and the expected position (desired value) of the virtual master function; and stretching of the said web of material in response to any deviation between the said actual position (actual value) and the said expected position (desired value), with the aim of minimizing the said deviation.

The object is also achieved by means of an arrangement of the type described in the introduction, which arrangement is characterized in that the control unit is arranged to initiate a reading off of the actual position (actual value) of a virtual master function upon the said detection, which said master function consists of a cyclic clock where the number of cycles per product, or alternatively the number of products per cycle, consists of an integer, for comparison between the said actual position (actual value) and the expected position (desired value) of the virtual master function, and is arranged to stretch the said web of material in response to any deviation between the said actual position (actual value) and the said expected position (desired value), with the aim of minimizing the said deviation.

By means of the disclosure, certain important benefits are obtained. Primarily, it can be noted that the disclosure results in a simple and clear control process for the synchronization of printed motifs. This applies in particular as the abovementioned comparison between a detected position and an expected position for the respective synchronization marks can be realized as a software-based model and not in the form of a quantity of measurements and control procedures in connection with the actual manufacturing process. This software-based model consists of a virtual master function, i.e. a periodic reference function, the actual position of which is compared with a required desired value when a synchronization mark is detected along the said web of material. In this way, a synchronization of the actual web of material is made possible by means of a fixed stationary desired value. This results in a simple and robust system.

The disclosure also results in a reduced risk of measuring inaccuracies that could otherwise arise through measurements and control functions being carried out at different stages in the manufacturing process.

BRIEF DESCRIPTION OF DRAWINGS

The invention will be described in the following in association with preferred embodiments and the attached drawings, in which.

DETAILED DESCRIPTION OF PREFERRED EMBODIMENTS

Figure 1:
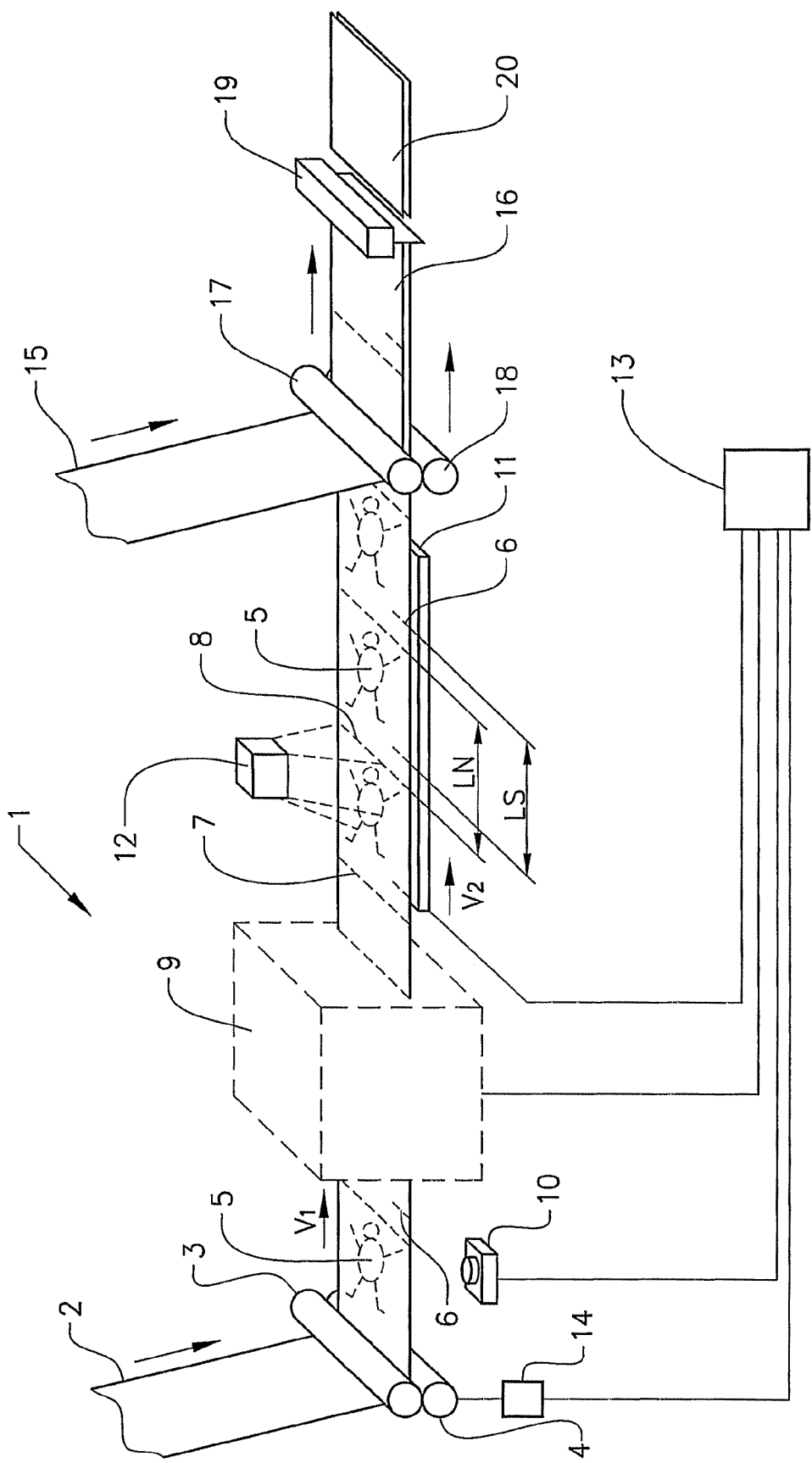
FIG. 1 is a schematic view of an arrangement arranged in accordance with a preferred embodiment of the present invention.

FIG. 1 is a schematic and simplified view of an arrangement 1 for manufacturing absorbent products, that is arranged in accordance with a preferred embodiment of the present invention. More specifically, the arrangement 1 is arranged for manufacturing absorbent products that start out as a first essentially continuous web of material 2, which is fed forward in a known way from a roll (not shown) or the like, in a direction that is indicated by an arrow in FIG. 1.

According to the preferred embodiment, the first web of material 2 consists of a backing layer for a disposable diaper, that is a material of the type that is non-permeable to liquid or that has at least a high resistance to the penetration of liquid, but which, however, is breathable. For this purpose, the first web of material 2 consists suitably of a thin and waterproof plastic film of, for example, polyethylene, polypropylene or polyester. Alternatively, a laminate of non-woven material and plastic film or other suitable and previously-known layers of material can be utilized as a liquid-tight backing layer.

The first web of material 2 can be fed forward by means of two rollers 3, 4 which are arranged to give the first web of material 2, that will become the backing layer, a certain given feed speed $v_1$.

FIG. 1 also shows that the first web of material 2 is processed in such a way that it comprises a printed motif 5. This motif 5 is suitably pre-printed on the first web of material 2. In addition, the motif 5 is applied in such a way that it recurs at a certain predetermined distance in such a way that one and the same motif is provided on each individual product that is manufactured from the first web of material 2. In addition, the motif 5 is indicated by broken lines in FIG. 1 to indicate that it is printed on the underside of the first web of material 2. In the finished product, the final position of the printed motif 5 will thus be in a predetermined position on the back of the product.

The motif 5 is printed at certain given regular intervals and is intended to be synchronized, which means that the final position of the motif 5 is intended to be in the same position on each individually manufactured product of the type in question. For this purpose, the first web of material 2 is provided with a number of reference marks or synchronization marks 6, suitably in the form of relatively short lines that are suitably pre-printed onto the first web of material 2. In the embodiment shown in FIG. 1, the synchronization marks 6 are printed on the underside of the first web of material 2. The invention is not, however, restricted to this, but it is possible to print the synchronization marks 6 on both sides of the first web of material 2.

In FIG. 1, the synchronization marks 6 are also indicated by broken lines, in order to indicate that they are printed on the underside of the first web of material 2. As will be described in detail below, the object of each synchronization mark 6 is to constitute a detectable reference element, by means of which various work elements and process steps that are carried out by means of the arrangement 1 are synchronized correctly in relation to each printed motif 5. In this way, the motif 5 can be positioned in the correct position on the finished product.

In the embodiment that is shown in FIG. 1, a processed element in the first web of material 2 is utilized, in the form of a printed motif 5. It should, however, be noted that the principle behind the invention is not limited to only the case when a printed motif is utilized. In other words, the invention can also be used for other positioned elements in the form of patterns, embossing, applications and ornamentation that constitute processing of the first web of material 2. Similarly, the principle behind the invention can be used for elements that consist of embossed patterns, folds, notches, holes and similar elements that are intended to be positioned in a predetermined, that is "synchronized", way on a finished product.

As shown in FIG. 1, the first web of material 2 can be divided into a certain nominal division length $L_N$, that is a length that is defined between two transverse positions 7, 8 that delimit a particular product. According to the embodiment that is shown in FIG. 1, the nominal division length $L_N$ consists in particular of a product length that corresponds to the front edge and back edge of a finished product. These positions 7, 8 are indicated by broken lines in FIG. 1. However, these lines are not printed on the first web of material 2.

Each printed motif 5 is placed in a position that is in a given and predetermined relationship to the respective synchronization mark 6. This means that each synchronization mark 6 is printed at a regularly recurring distance $L_S$ that corresponds to the periodicity of the printed motif 5.

As shown in FIG. 1 in a schematic and simplified way, the first web of material 2 is fed through a processing apparatus 9 where a number of work elements and process steps are carried out in a way that is already known. These work elements can comprise, for example, the application of various types of absorbent material, wadding material and the like, and any other material and components such as, for example, elastic, adhesive tape and the like. The work elements that are carried out in the processing apparatus 9 can also comprise folding, cutting, ultrasound welding and other processing steps. The manufacture of absorbent products by means of a series of such work elements is already known, and for this reason will not be described here in detail. As an example, however, reference can be made to the said patent document WO 00/59429 mentioned in the introduction, that describes an example of a previously-known manufacturing process for absorbent products.

Still with reference to FIG. 1, it can be noted that the first web of material 2 has passed a detecting device 10 just before it is fed into the processing apparatus 9. In a way that will be described in detail below, the detecting device 10 is arranged to detect the presence of each synchronization mark 6. The feeding of the first web of material 2 is carried out by means of a feeding device that preferably consists of a suction conveyor 11 which is a known feeding device that can be controlled to feed forward the first web of material 2 at a given feed speed $v_2$. In addition, the first web of material 2 is fed past a gluing station 12 at which adhesive is applied in order to enable a subsequent outer layer to be glued on, in the way that will be described below.

The detecting device 10 consists preferably of a suitable device for optical inspection, according to the embodiment in the form of a video camera that is arranged in association with the first web of material 2. The detecting device 10 is arranged in such a way that it continually inspects and records images along the underside of the first web of material 2 as shown schematically in FIG. 1. For this purpose, the detecting device 10 comprises a set of light-sensitive elements, by means of which it records the light transmission from the first web of material 2 while this is moved in relation to the detecting device 10.

In addition, the detecting device 10 is connected to a computer-based control unit 13. Information from the detecting device 10 is transmitted in this way to the control unit 13, which in turn is provided with software for image processing that is arranged to detect each synchronization mark 6 that passes over the detecting device 10. In addition, the control unit 13 is connected, in a way that will be described in detail below, to a speed-control device 14 for controlling the speed $v_1$ at which the first web of material 2 is fed forward. The control unit 13 is also connected to the suction conveyor 11 for controlling the speed $v_2$ of this.

According to an alternative embodiment, the detecting device 10 can be, for example, a CCD camera ("charged coupled device"), i.e. with a set of light-sensitive sensors arranged in one or more rows. By means of this arrangement, the position of each synchronization mark 6 can be detected. According to yet another alternative embodiment, the detecting device can be based on, for example, laser technology, that is with a laser light source that is utilized in conjunction with a light-sensitive detector to detect the position of each synchronization mark 6. According to yet another variant, the synchronization mark can consist of an electronically detectable sensor, for example of the transponder type, that is applied on the first web of material 2 and with the abovementioned regular intervals $L_S$. Such a synchronization mark can then be read by a detecting device that comprises a radio transmitter and radio receiver for this purpose in a known way. According to yet another alternative embodiment, the said synchronization marks can be printed with magnetic ink that can then be detected by a sensor that detects magnetism.

When the first web of material 2 has been fed past the detecting device 10, it meets a second web of material 15, according to the embodiment in the form of an essentially liquid-permeable layer that is intended to form an outer layer of the finished product. For this reason, the second web of material 15 consists suitably of a non-woven material with a soft and smooth surface, such as, for example, a spun bond material of polypropylene fibre. Other examples of materials that are suitable for constituting the outer layer are perforated plastic films, such as, for example, a perforated polyester film.

The second web of material 15 is thus joined to the first web of material 2 (together with any additional layers of material and other components that are added in association with the processing apparatus 9 as described above) for example by means of the adhesive that was previously applied at the gluing station 12. In this way, a complete web of material 16 is created, intended to define a number of manufactured products, which is fed forward in a direction that is indicated by an arrow in FIG. 1 and taken up and fed forward by means of additional driving units, for example in the form of two rotating feeding rollers 17, 18 arranged respectively over and under the complete web of material 16. In this way, the complete web of material 16 can be fed forward.

After the assembly with the second web of material 15, a complete continuous web of material 16 is thus created, consisting of a number of finished absorbent products that are still joined together. This web of material 16 is finally fed past a cutting station 19, suitably of the "cross-cutter" type, where cutting is carried out at positions that essentially correspond to the imaginary boundary lines 7, 8 for each finished product. In this way, a number of finished products are created in the form of absorbent products 20.

With reference again to the detecting device 10, it can be noted in particular that it is arranged to detect the position of each synchronization mark 6. Information regarding a detected position for a given synchronization mark 6 is then used for various process steps that, for example, are carried out in the processing apparatus 9 in order to ensure that the printed motif 5 is always positioned in a correct position on each finished product 20. For this purpose, the control unit 13 is arranged with a virtual data-based reference function or master function, which will now be described with reference initially to FIG. 2*a*.

Figure 2A:
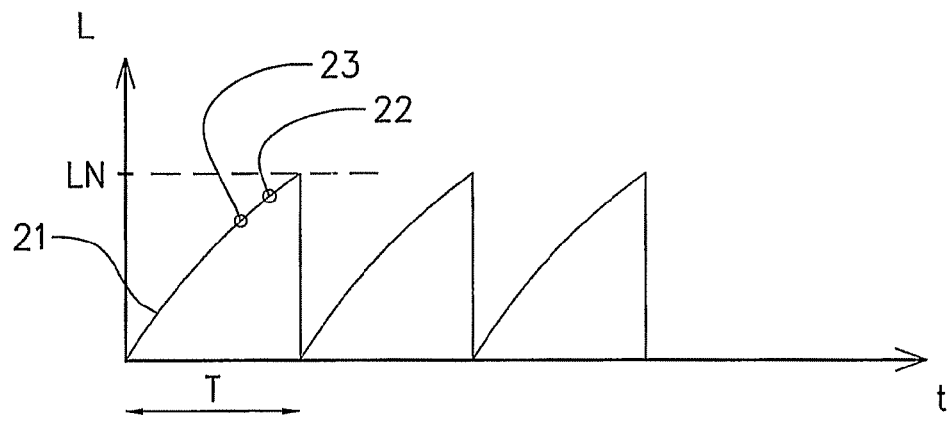
FIG. 2a is a diagram that shows a control function in accordance with a preferred embodiment of the invention.

The virtual master function is a cyclic clock that preferably turns one revolution per product 20. As described in detail below, the master function is not limited to only to this periodicity. An event-controlled reading off of this clock can be interpreted as the relative position of the event in question in relation to a fixed point on the product in question, that is in relation to a type of virtual zero point or reference for the product. FIG. 2*a* shows the virtual master function in the form of a ramp-like curve 21 that recurs at regular intervals.

The detecting device 10 is utilized first to detect a particular synchronization mark 6 along the first web of material 2. When a synchronization mark 6 is found, the control unit 13 is used to detect in what position along the virtual master function 21 the synchronization mark 6 is located. Information about the actual position of the virtual master function 21 is thus recorded by means of the control unit 13. Thereafter, the control unit 13 compares the actual position of the virtual master function (actual value) with an expected position (desired value). The speed $v_1$ of the first web of material 2 is then changed in relation to the speed $v_2$ of the suction conveyor 11 in response to any deviation between the actual position and the expected position. The slower the speed $v_1$ in comparison with $v_2$, the more the material in the first web of material 2 will be stretched. This is then utilized to obtain a correct synchronization of the first web of material 2.

FIG. 2*a* shows the said master function or reference function in the form of a ramp-like curve 21 that recurs at regular intervals and that symbolizes a periodic clock that is utilized for detecting each synchronization mark 6. For this reason, the curve 21 is drawn in an xy-coordinate system where the x-axis corresponds to the time t, and where a period in the curve 21 corresponds to the time T that it takes for a nominal division length $L_N$ of the material in question to pass the detecting device 10. In addition, the y-axis corresponds to a length L for the first web of material 2, with a maximal value $L_N$ of the curve 21 corresponding to the length of each product. The curve 21 indicates in a schematic way a rise from a zero value that indicates one end of a product to a maximal value $L_N$ that indicates the other end of the product and that, according to the described embodiment, corresponds to the length of the product.

A value of the position of the virtual master function that has been read off (when a synchronization mark 6 has just been detected) is thus compared periodically with an expected position along the virtual master function. The expected value, that is the desired value, is indicated in FIG. 2 by the reference numeral 22 and corresponds to the printed motif 5 being positioned correctly in its intended place on the finished product. The precise position for this desired value 22 is determined by a number of factors, such as, for example, the equipment comprised in the arrangement 1, the dimensions of the comprised material, the process speed, etc. The curve 21 with its desired value 22 thus consists of predefined data that is stored in the control unit 13. For this reason, the reference function or master function that is illustrated by the curve 21 can be said to be "virtual", as it is generated and stored in the form of software in the control unit 13.

Figure 2B:
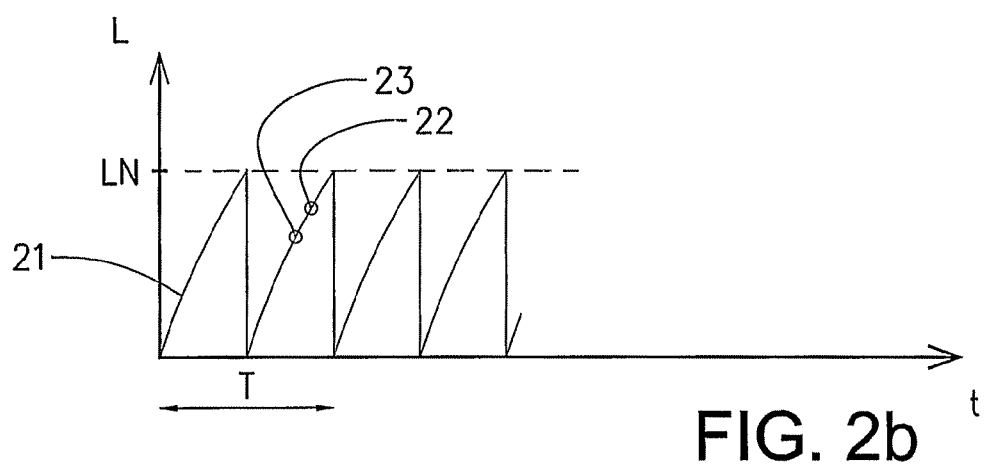
FIG. 2b is a diagram that shows an alternative control function.
Figure 2C:
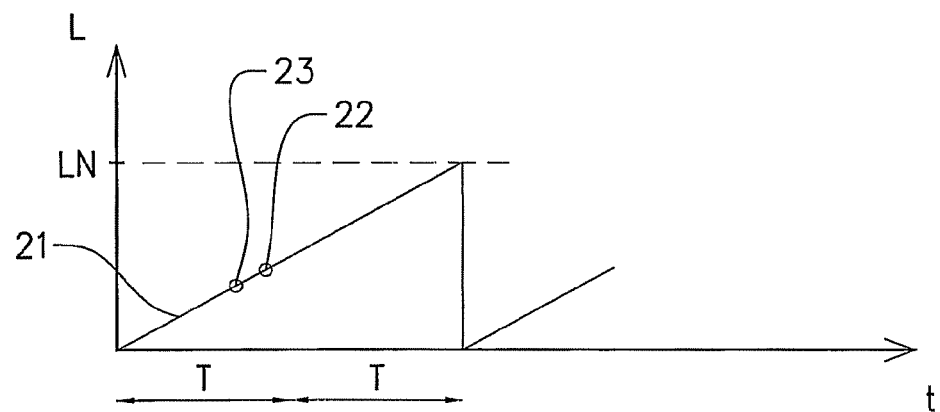
FIG. 2c is a diagram that shows yet another alternative control function.

FIG. 2*b* shows an alternative embodiment, in which the virtual master function 21 is arranged in such a way that two periods in the curve 21 correspond to the time T that it takes for a nominal division length $L_N$ of the material in question to pass the detecting device 10. FIG. 2*c* shows yet another embodiment in which the virtual master function 21 is arranged in such a way that a period in the curve 21 corresponds to twice the time T that it takes for a nominal division length $L_N$ of the material in question to pass the detecting device 10.

Taken as a whole, as illustrated by FIGS. 2*a*, 2*b* and 2*c*, a basic principle is that the master function 21 consists of a cyclic clock where the number of cycles T per product 20, or alternatively the number of products 20 per cycle T, consists of integers. In all the embodiments that are shown in FIGS. 2*a*, 2*b* and 2*c*, the principle is used that detection of a given synchronization mark 6 is carried out using the detecting device 10. This results in the recording of a position along the curve 21 that corresponds to this detected synchronization mark 6. This position then constitutes an actual value that is indicated schematically by the reference numeral 23 in FIGS. 2*a*, 2*b*, 2*c*. As the length of the period T for the curve 21 can be said to have a given relationship to the product length of each product, the actual value 23 will consist of a numerical value corresponding to a certain proportion of the total product length.

In addition, the control unit 13 is arranged to compare the desired value 22 and the actual value 23 (that is the actual position) that was recorded during the detection of a particular synchronization mark 6. According to the examples that are shown in FIGS. 2*a*, 2*b* and 2*c*, there is a difference between the desired value 22 and the actual value 23. This difference can be expressed as a difference between the proportion of the whole product length that corresponds to the desired value 22 minus the proportion of the product length that corresponds to the actual value 23. If there is a relatively large difference between the desired value 22 and the actual value 23 (as shown in, for example, FIG. 2*a*), the printed motif 5 would be positioned on the first web of material 2 displaced somewhat in relation to its intended position, that is the motif 5 would not then be correctly synchronized. For this reason, it is an underlying principle that the position of the printed motif 5 on the finished product 20 is adjusted by stretching the first web of material 2 if there is such a deviation between the desired value 22 and the measured value 23. For this reason, the synchronization marks 6 are pre-printed on the first web of material 2 in such a way that they recur at regular intervals $L_S$ that are somewhat shorter than the intended product length $L_N$. This means that the distance $L_S$ between two consecutive synchronization marks 6 is shorter than the product length $L_N$, which in turn corresponds to the intended final length of the finished product 20. The fact that the distance $L_S$ between two synchronization marks 6 is shorter than the product length $L_N$ makes it possible to stretch the first web of material 2 to a certain extent, in order in this way to position the printed motif 5 so that, in its final position, it is in the correct position on the finished product 20.

According to the embodiment shown, the abovementioned stretching of the first web of material 2 is achieved by a control of the speed of the first speed-control device 14, which in turn controls the feed speed $v_1$ for the first web of material 2. More specifically, the control unit 13 is arranged to control the speed-control device 14 in such a way that the first web of material 2 is given a speed $v_1$ that is somewhat lower than the speed $v_2$ of the suction conveyor 11. This leads in turn to a stretching of the material in the first web of material 2 when it runs through the process apparatus 9. In this way, the position of the printed motif 5 on the finished product and thereby also the position of the respective synchronization mark 6, is adjusted in such a way that the deviation between the desired value 22 and the actual value 23 relating to the position of the synchronization mark 6 is eliminated.

According to the embodiment, the distance $L_S$ between two consecutive synchronization marks 6 is of the order of 2% shorter than the product length $L_N$. This makes it possible to utilize the natural elasticity of the first web of material 2 for stretching it in accordance with the abovementioned principles. The invention is, however, not limited to any specific ratio between the product length $L_N$ and the distance between synchronization marks $L_S$, but instead this ratio can vary, depending upon the comprised material and which type of process apparatus is utilized. Nor is the invention limited to the nominal division lengths having to be connected to the product length, but instead other divisions of the first web of material 2 are possible within the framework of the invention.

To sum up, the disclosure is based on a detection of synchronization marks 6, the position of which is detected and utilized for synchronizing a printed motif 5 in the correct intended position on a finished product. The synchronization is carried out using a virtual reference function or "master" function that is stored in the control unit 13 and that is arranged to provide references in order to make it possible to stretch the first web of material 2 if a deviation is recorded between an actual position and the expected position of each synchronization mark 6. In this way, a simple and accurate process is obtained for synchronizing the printed motif 5.

The invention is not limited to what is described above, various embodiments being possible within the framework of the patent claims. For example, the invention is particularly suitable for use in association with a manufacturing process for making absorbent products such as diapers, incontinence pads, sanitary towels and panty liners, but is not limited only to this type of product, being able, in principle, to be utilized in other manufacturing processes that are based on an essentially continuous web of material being divided into a certain product length and where a printed motif or other similar process is synchronized in the correct position.

The invention is particularly suitable for use with the applications where the first web of material 2 consists of a material intended to form a backing layer in a diaper. Such a material then consists suitably of a plastic film that is non-permeable to liquid, which is suitable for the abovementioned stretching procedure and is also suitable for printing with high quality colour motifs. The invention can, however, be used with other material than just the backing layer for diapers, for example other elastic and stretchable webs of material, for example non-woven material, that is fibrous materials with fibres such as for example polyolefins, that is polymer material such as polyethylene and polypropylene, or alternatively polyester, nylon or the like. The invention can also be utilized when the first web of material consists of some other type of synthetic or textile material. The invention can also be used for different types of laminates comprising varying numbers of layers of material.

Regarding the printed motif 5, this can be provided by being pre-printed onto the first web of material 2. Alternatively, the actual manufacturing process that is obtained with the process apparatus 9 can comprise a process for printing the motif.

In addition, it can be noted, with reference to FIG. 2, that a period length T in the reference function 21 can correspond to a product length, as described above. Alternatively, a period length T can correspond to two or more product lengths, or a certain proportion of a product length. This means that the synchronization marks can be positioned in a corresponding way, for example in every other position in comparison with what is shown in FIG. 1.

With reference to FIG. 2, it can be pointed out that the invention is not limited to a virtual master function where a period corresponds clearly to a product length. Alternatively, the invention can be arranged in such a way that a given product length corresponds to two or more synchronization marks and thus also two or more periods in the virtual master function.

The invention claimed is:

1. A method for synchronized positioning of at least one essentially continuous web of material, for manufacturing products that comprise printed motifs or processed elements, which web of material is adapted to be divided into nominal division lengths and comprises synchronization marks that recur at regular intervals, which method comprises:
    feeding the web of material into a production apparatus at a first speed;
    processing the web material in the production apparatus with various process steps for the manufacture, with the web of material being fed forward at a second speed; and
    detecting each synchronization mark, each synchronization mark for positioning a respective one of the printed motifs in a predetermined position on each product;
    generating a virtual master function which includes a cyclic clock where a number of cycles per product, or alternatively a number of products per cycle, consists of an integer, and reading an actual value in the virtual master function corresponding to a detected synchronization mark;
    comparing the actual value with an expected value of the virtual master function, the expected value corresponding to an intended position of a synchronization mark; and
    stretching the web of material in response to any deviation between the actual value and the expected value, with an aim of minimizing the deviation.

2. The method according to claim 1, wherein the virtual master function is generated and stored in a computer-based control unit.

3. The method according to claim 1, wherein the regular interval between the synchronization marks is 2% shorter than the nominal division length.

4. The method according to claim 1, wherein the stretching is achieved by a control of the first speed to a lower value than the second speed.

5. The method according to claim 1, wherein the nominal division length consists of a predetermined product length for the product.

6. The method according to claim 1, wherein the product is an absorbent product and in the method comprises the provision of a web of material in the form of a layer for the absorbent product.

7. The method according to claim 6, wherein the web of material is a backing layer for the product.

8. The method according to claim 6, wherein the web of material comprises a side panel, a top layer, or wadding material components in the product.

9. The method according to claim 6, wherein the web of material consists of a side panel in the product.

10. The method according to claim 1, wherein the method further comprises:
    feeding out of a complete web of material that comprises a continuous row of a number of products; and
    cutting of the complete web of material into individual products with the nominal division length.

11. An arrangement for synchronized positioning of at least one essentially continuous web of material for manufacturing products that comprise printed motifs or processed elements, which web of material is adapted to be divided into nominal division lengths and comprises synchronization marks that recur at regular intervals, which arrangement additionally comprises:
- a first speed-control device for feeding the web of material into a production apparatus at a first speed, which production apparatus is arranged to carry out various process steps for the manufacture;
- a second speed-control device for feeding the web of material through the process steps at a second speed;
- a detector for detecting the respective synchronization marks; and
- a computer-based control unit arranged for the synchronization, whereby the respective motifs are positioned in a predetermined position on each product, wherein the control unit is arranged to initiate a reading of the actual value of a virtual master function upon the detection, which master function includes a cyclic clock where a number of cycles per product, or alternatively a number of products per cycle, consists of an integer, for comparison between the actual value and an expected value of the virtual master function, and for stretching the web of material in response to any deviation between the actual value and the expected value, with an aim of minimizing the deviation.

12. The arrangement according to claim 11, wherein the master function is stored in the form of software in the control unit.

13. The arrangement according to claim 11, wherein the regular interval between the synchronization marks is 2% shorter than the nominal division length.

14. The arrangement according to claim 11, wherein the control unit is arranged to carry out the stretching by a control of the first speed-control device and the second speed-control device so that the first speed is given a lower value than the second speed.

* * * * *